(12) United States Patent
Shin et al.

(10) Patent No.: US 11,603,526 B2
(45) Date of Patent: Mar. 14, 2023

(54) PATHOGEN LYSIS AND NUCLEIC ACID EXTRACTION METHOD USING ZINC OXIDE NANOSTAR

(71) Applicant: INFUSION TECH, Anyang-si (KR)

(72) Inventors: Yong Shin, Seoul (KR); Huifang Liu, Ulsan (KR)

(73) Assignee: INFUSION TECH, Anyang-si (KR)

( * ) Notice: Subject to any disclaimer, the term of this patent is extended or adjusted under 35 U.S.C. 154(b) by 267 days.

(21) Appl. No.: 16/759,366

(22) PCT Filed: Oct. 18, 2018

(86) PCT No.: PCT/KR2018/012339
§ 371 (c)(1),
(2) Date: Apr. 27, 2020

(87) PCT Pub. No.: WO2019/088527
PCT Pub. Date: May 9, 2019

(65) Prior Publication Data
US 2020/0291387 A1 Sep. 17, 2020

(30) Foreign Application Priority Data

Oct. 30, 2017 (KR) .................. 10-2017-0142590
Oct. 18, 2018 (KR) .................. 10-2018-0124184

(51) Int. Cl.
*C12N 15/10* (2006.01)
*C12Q 1/6806* (2018.01)

(52) U.S. Cl.
CPC ....... *C12N 15/1006* (2013.01); *C12Q 1/6806* (2013.01)

(58) Field of Classification Search
CPC .... C12N 15/1006; C12N 1/06; C12Q 1/6806; C12Q 2563/155
USPC ...................................................... 536/25.4
See application file for complete search history.

(56) References Cited

U.S. PATENT DOCUMENTS

| 2007/0178478 | A1 | 8/2007 | Dhallan et al. |
| 2015/0322486 | A1 | 11/2015 | Shin et al. |
| 2016/0215325 | A1* | 7/2016 | Kshirsagar ............... C12Q 1/24 |

FOREIGN PATENT DOCUMENTS

| KR | 10-2010-0134554 A | 12/2010 |
| KR | 10-2015-0096444 A | 8/2015 |
| KR | 10-2015-0142492 A | 12/2015 |
| WO | 2007/070381 A2 | 6/2007 |
| WO | 2015/195949 A2 | 12/2015 |
| WO | 2018/200202 A1 | 11/2018 |

OTHER PUBLICATIONS

Kwong et al, Journal of Nanomaterials, 2015, 1-9.*
Ragupathy et al., Langmuir, 2011, 27, 4020-4028.*
Tian et al, DIT Biophotonics and Imaging, 2015, 1-40.*
Shin et al, Lab Chip, 2014, 14, 359-368.*
International Search Report for PCT/KR2018/012339 dated May 22, 2019 from Korean Intellectual Property Office.
Xie, Y. et al., "Antibacterial Activity and Mechanism of Action of Zinc Oxide Nanoparticles against Campylobacter jejuni", Appl. Environ. Microbiol. Feb. 4, 2011, vol. 77, No. 7, pp. 2325-2331.
Tian, F. et al., "Investigating the Role of Shape on the Biological Impact of Gold Nanoparticles in Vitro", Nanomedicine. Sep. 7, 2015, vol. 10, No. 17, pp. 2643-2647.
Zhao, F. et al., "A single-tube approach for in vitro diagnostics using diatomaceous earth and optical sensor", Biosensors and Bioelectronics, vol. 99, Jan. 15, 2018, pp. 443-449.
A.Król et al, "Zinc oxide nanoparticles: Synthesis, antiseptic activity and toxicity mechanism", Advances in Colloid and Interface Science, vol. 249, Nov. 2017, pp. 37-52.
Amna Sirelkhatim et al, "Reviewon Zinc Oxide Nanoparticles: Antibacterial Activity and Toxicity Mechanism", Nanomicro Letters, vol. 7, No. 3, Apr. 19, 2015, pp. 219-242.
Thomas J Webster et al, "Antimicrobial applications of nanotechnology: methods and literature", Int J Nanomedicine, vol. 20127, Jan. 1, 2012, pp. 2767-2781.
Krishna R Raghupathi et al, "Size-Dependent Bacterial Growth Inhibition and Mechanism of Antibacterial Activity of Zinc Oxide Nanoparticles", Langmuir, vol. 27, No. 7, Apr. 5, 2011, pp. 4020-4028.
Nicole Jones et al, "Antibacterial activity of ZnO nanoparticle suspensions on a broad spectrum of microorganisms", FEMS Microbiology Letters, vol. 279, No. 1, Feb. 1, 2008, pp. 71-76.
Nagarajan Padmavathy et al, "Enhanced bioactivity of ZnO nanoparticles-an antimicrobial study", Science and Technology of Advanced Materials, Jul. 1, 2008, pp. 035004-035007.
Tony Jin et al, "Antimicrobial Efficacy of Zinc Oxide Quantum Dots against Listeria monocytogenes, *Salmonella enteritidis*, and *Escherichia coli* O157:H7", Journal of Food Science, vol. 74, No. 1, Jan. 1, 2009, pp. M46-M52.
Y Liu et al, "Antibacterial activities of zinc oxide nanoparticles against *Escherichia coli* O157:H7", Journal of Applied Microbiology, vol. 107, No. 4, Oct. 1, 2009, pp. 1193-1201.
Zarrindokht Emami-Karvani et al, "Antibacterial activity of ZnO nanoparticle on Gram-positive and Gram-negative bacteria", African Journal of Microbiology Research vol. 5(12), pp. 1368-1373, Jun. 18, 2011.

* cited by examiner

*Primary Examiner* — Ganapathy Krishnan
(74) *Attorney, Agent, or Firm* — Revolution IP, PLLC

(57) ABSTRACT

The present invention relates to a method for lysing pathogen lysis and a method for extracting nucleic acid using zinc oxide nanostar, and the method for extracting nucleic acid using zinc oxide nanostar according to the present invention can extract nucleic acids by lysing cells of a pathogen without using a lysis buffer and can extract nucleic acid of high-purity and high-concentration by preventing nucleic acid degradation and fragmentation through various substances including salts contained in the lysis buffer at high concentration. In addition, the zinc oxide nanostar of the present invention (200 to 900 nm) has superior cell lysis capacity compared to the conventional zinc oxide nanoparticles (20 to 50 nm), thereby increasing the nucleic acid extraction efficiency and can extract at room temperature without a heating step to use as a field diagnostic method.

3 Claims, 7 Drawing Sheets

FIG. 7
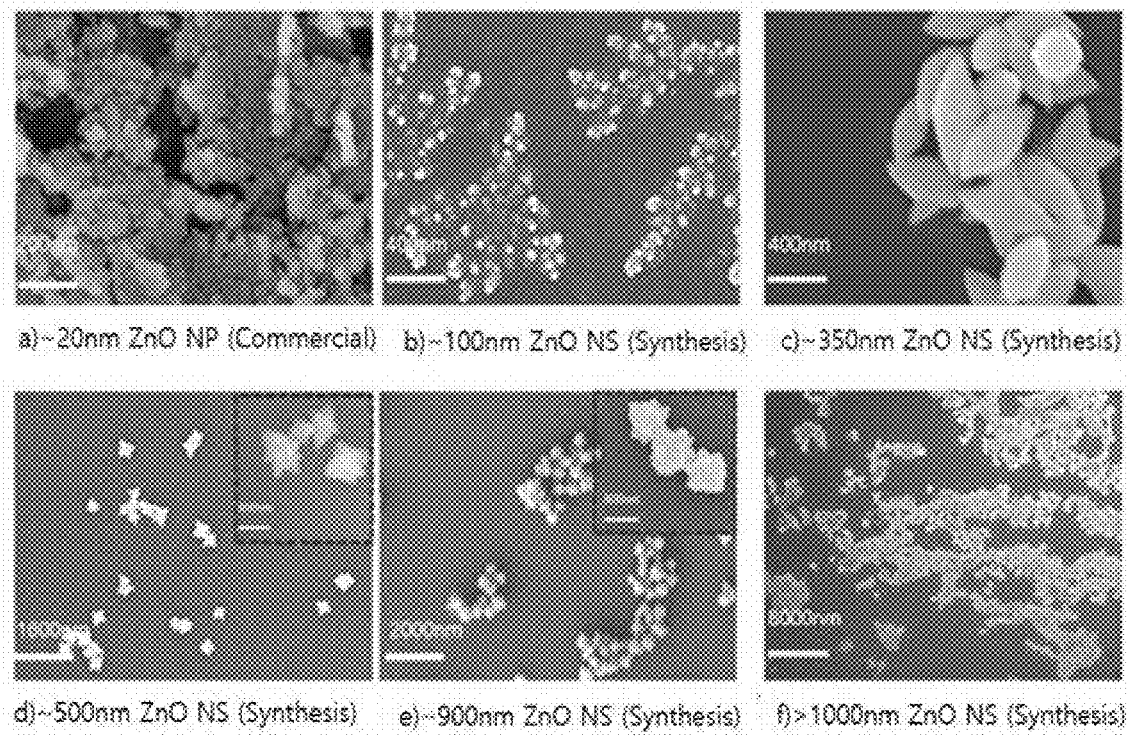
a) ~20nm ZnO NP (Commercial)  b) ~100nm ZnO NS (Synthesis)  c) ~350nm ZnO NS (Synthesis)
d) ~500nm ZnO NS (Synthesis)  e) ~900nm ZnO NS (Synthesis)  f) >1000nm ZnO NS (Synthesis)
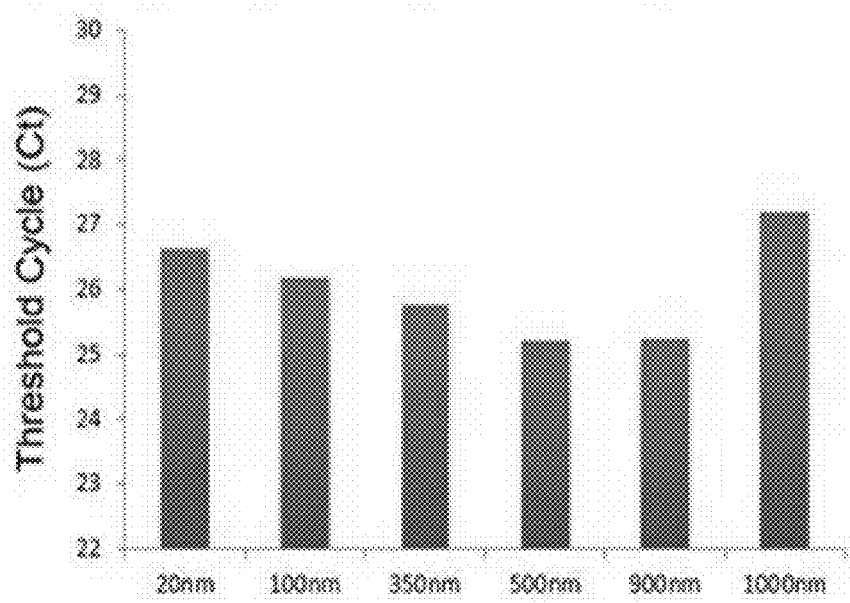

PATHOGEN LYSIS AND NUCLEIC ACID EXTRACTION METHOD USING ZINC OXIDE NANOSTAR

TECHNICAL FIELD

The present invention relates to a method for lysing pathogen and extracting nucleic acid using zinc oxide nanostar.

BACKGROUND ART

Nucleic acids are an important analytical tool for identifying disease states, and DNA biomarkers such as single nucleotide polymorphism (SNP), mutations or DNA methylation can help researchers find the cause of cancer, diagnose and observe the condition of the disease during the early stages of the disease, which provides important clues to give great opportunities for prognosis and surveillance.

Nucleic acids such as DNA are present at very low physiological concentrations compared to other components such as proteins (e.g. tens of nanograms of DNA per microliter of whole blood versus tens of micrograms of protein), effectively extracting DNA from clinical samples and pre-concentration is very important for subsequent processes such as amplification and detection. In the case of methylated DNA, this problem is even more important.

Recently, as more and more purified nucleic acids are used in various fields such as diagnostic medicine, pharmacy medicine, metabolic medicine including biotechnology, efforts to isolate nucleic acids from various biological samples more rapidly and purely have continued.

However, the biggest advancement in the method of isolating nucleic acids up to now has been directed to carriers that specifically adsorb only nucleic acids from various types of substances contained in cell lysis solutions, such as genomic DNA, plasmid DNA, messenger RNA, proteins, and cell debris particles. The focus of almost all research, including this technology, has been limited to research and development of substances adsorbing nucleic acids.

Accordingly, in order to separate nucleic acids from various biological samples more quickly and purely, it is urgent to develop a technology capable of quickly separating only desired nucleic acids from cell debris particles, protein denatured aggregates and other various cell degradation substances.

DISCLOSURE

Technical Problem

An object of the present invention is to provide a composition for lysing pathogen comprising zinc oxide nanostar, a method for lysing pathogen and kit using the same; a composition for extracting nucleic acid comprising zinc oxide nanostar, and a method for extracting nucleic acid and kit using the same.

Technical Solution

In order to achieve the above object, the present invention provides a composition for lysing pathogen comprising zinc oxide nanostar.

Also, the present invention provides a kit for lysing pathogen comprising the composition.

In addition, the present invention provides a method for lysing pathogen comprising contacting a zinc oxide nanostar with a sample containing a pathogen.

In addition, the present invention provides a composition for extracting nucleic acid comprising zinc oxide nanostar.

Furthermore, the present invention provides a kit for extracting nucleic acid comprising the composition.

In addition, the present invention provides a method for extracting nucleic acid comprising: a first step of preparing a mixture by adding zinc oxide nanostar to a nucleic acid sample and reacting; and a second step of extracting the nucleic acid from the mixture.

In addition, the present invention provides a method for extracting nucleic acid comprising: a first step of preparing a mixture by adding zinc oxide nanostar to a nucleic acid sample and reacting; a second step of preparing a reaction mixture by adding a diatomaceous earth modified with a silane compound to the mixture and adding at least one selected from the group consisting of dimethyl adipimidate (DMA), dimethyl pimelimidate (DMP), dimethyl suberimidate (DMS) and dimethyl 3,3'-dithiobispropionimidate (DTBP); and a third step of extracting the nucleic acid from the reaction mixture.

Advantageous Effects

The method for extracting nucleic acid using zinc oxide nanostar according to the present invention can extract nucleic acids by lysing cells of a pathogen without using a lysis buffer and can extract nucleic acid of high-purity and high-concentration by preventing nucleic acid degradation and fragmentation through various substances including salts contained in the lysis buffer at high concentration. In addition, the zinc oxide nanostar of the present invention (200 to 900 nm) has superior cell lysis capacity compared to the conventional zinc oxide nanoparticles (20 to 50 nm), thereby increasing the nucleic acid extraction efficiency and can extract at room temperature without a heating step to use as a field diagnostic method.

DESCRIPTION OF DRAWINGS

FIG. 7 shows a comparison of the nucleic acid extraction efficiency of zinc oxide nanostar according to the particle size using colon cancer cell line HCT116.

BEST MODE

Figure 1:
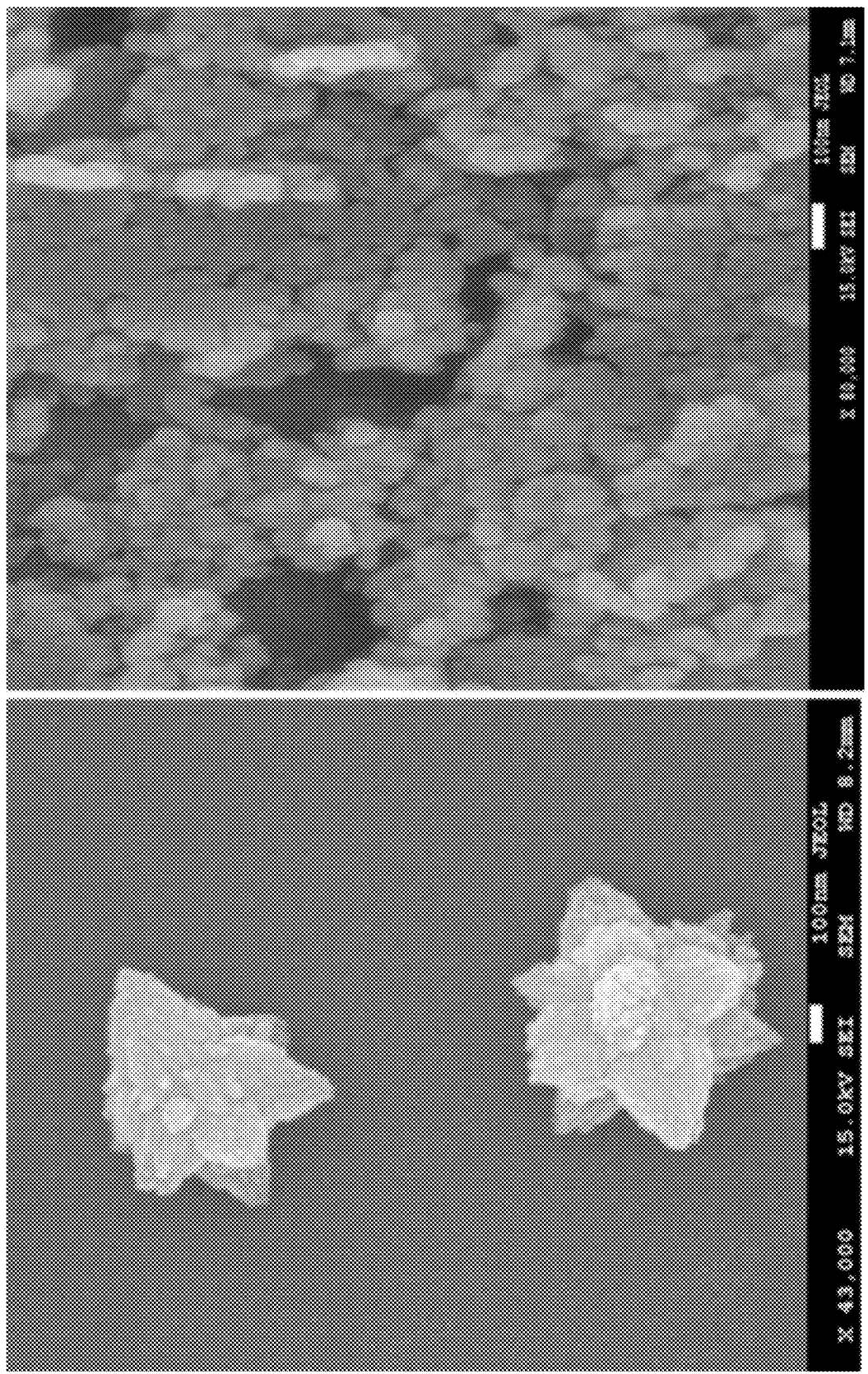
FIG. 1 shows a comparison of the size and shape of zinc oxide nanostars (A) and zinc oxide nanoparticles (B).

Hereinafter, the present invention will be described in more detail.

The inventors of the present invention have developed an extraction method capable of lysing pathogens and extracting nucleic acids and found that the zinc oxide nanostar (ZnO NS) of the present invention can extract high-concentration nucleic acids by having a size and shape capable of increasing the lytic capacity of cell membranes and nuclei of pathogens compared to conventional zinc oxide nanoparticles and also that the method for extracting nucleic acid using zinc oxide nanostar of the present invention can extract nucleic acids with high purity and high concentration without lysis buffer and heating step, thereby being capable of the on-the-spot diagnosis and completed the present invention.

The present invention provides a composition for lysing pathogen comprising zinc oxide nanostar.

The zinc oxide nanostar refers to nanoparticles in which a plurality of pointed protrusions is arranged in a ring.

The zinc oxide nanostar may have an average particle diameter of 200 to 900 nm, preferably, an average particle diameter of 350 to 900 nm, and more preferably, an average particle diameter of 500 nm, but it is not limited thereto.

The pathogen is a microorganism, and the microorganism may be a virus, bacteria, fungi, protozoa, *Rickettsia* or *spirochaeta*, but it is not limited thereto.

In addition, the present invention provides a kit for lysing pathogen comprising the composition.

In addition, the present invention provides a method for lysing pathogen comprising contacting a zinc oxide nanostar with a sample containing a pathogen.

The sample containing a pathogen may be any one selected from the group consisting of feces, urine, tears, saliva, external secretions from skin, external secretions from respiratory tract, external secretions from intestinal tract, external secretions from digestive tract, plasma, serum, blood, spinal fluid, lymph fluid, body fluids and tissues of object suspected of being infected with the pathogen, but it is not limited thereto.

The pathogen is a microorganism, and the microorganism may be a virus, bacteria, fungi, protozoa, *Rickettsia* or *spirochaeta*, but it is not limited thereto.

In addition, the present invention provides a composition for extracting nucleic acid comprising zinc oxide nanostar.

The zinc oxide nanostar refers to nanoparticles in which a plurality of pointed protrusions is arranged in a ring.

The zinc oxide nanostar may have an average particle diameter of 200 to 900 nm, preferably, an average particle diameter of 350 to 900 nm, and more preferably, an average particle diameter of 500 nm, but it is not limited thereto.

The nucleic acid may be DNA or RNA.

In addition, the present invention provides a kit for extracting nucleic acid comprising the composition.

In addition, the present invention provides a method for extracting nucleic acid comprising: a first step of preparing a mixture by adding zinc oxide nanostar to a nucleic acid sample and reacting; and a second step of extracting the nucleic acid from the mixture.

In addition, the present invention provides a method for extracting nucleic acid comprising: a first step of preparing a mixture by adding zinc oxide nanostar to a nucleic acid sample and reacting; a second step of preparing a reaction mixture by adding a diatomaceous earth modified with a silane compound to the mixture and adding at least one selected from the group consisting of dimethyl adipimidate (DMA), dimethyl pimelimidate (DMP), dimethyl suberimidate (DMS) and dimethyl 3,3'-dithiobispropionimidate (DTBP); and a third step of extracting the nucleic acid from the reaction mixture.

The silane compound may be a compound represented by the following Chemical Formula 1, but it is not limited thereto.

[Chemical Formula 1]

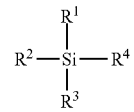

wherein each of $R^1$ to $R^3$ may be same or different, and are any one of C1 to C4 alkyl or C1 to C4 alkoxy, and $R^4$ is anyone of amino(C1 to C10) alkyl, 3-(2-amino (C1 to C4)alkylamino) (C1 to C4)alkyl or 3-[2-(2-amino (C1 to C4)alkylamino) (C1 to C4) alkylamino] (C1 to C4)alkyl.

The silane compound may be at least one selected from the group consisting of (3-aminopropyl) triethoxysilane (APTES), (3-aminopropyl)trimethoxysilane), (1-aminomethyl)triethoxysilane, (2-aminoethyl)triethoxysilane, (4-aminobutyl)triethoxysilane), (5- aminopentyl)triethoxysilane, (6-aminohexyl)triethoxysilane, 3-aminopropyl(diethoxy)methylsilane (APDMS), N-[3-(trimethoxysilyl)propyl]ethylenediamine, N-[3-(trimethoxysilyl)propyl] diethylenetriamine, [3-(2-aminoethylamino)propyl] trimethoxysilane (AEAPTMS) and 3-[(trimethoxysilyl) propyl]diethylenetriamine (TM PTA), but it is not limited thereto.

In addition, the present invention provides a method of preparing zinc oxide nanostar comprising: a first step of preparing a mixture by adding zinc nitrate hexahydrate and hexadecyltrimethylammonium bromide to water; a second step of preparing a reaction mixture by heating the mixture at 85 to 95° C. for 30 to 80 minutes; and a third step of preparing a colloidal solution by adding a ammonium hydroxide dropwise to the reaction mixture.

MODE FOR CARRYING OUT THE INVENTION

Hereinafter, the present invention will be described in more detail through examples. These examples are only intended to illustrate the present invention in more detail, and it will be apparent to those skilled in the art that the scope of the present invention is not limited by these examples according to the gist of the present invention.

Example 1: Chemicals and Reagents

All reagents were used without purification in analytical grade. Zinc nitrate hexahydrate (Zn $NO_3 \cdot 6H_2O$, 98%), ammonium hydroxide solution (28% of $NH_3$ in $H_2O$, based on 99.99% of trace metal) and (3-aminopropyl)triethoxysilane (APTES, 98%) were purchased from Sigma-Aldrich (St Louis, Mo., USA). Hexadecyltrimethylammonium bromide (=cetyltrimethylammonium bromide; CTAB) ($C_{19}H_{42}BrN$, >98%) was purchased from Tokyo Chemical Industry. Commercial zinc oxide nanoparticles (dispersion, 20 wt %, size less than 40 nm in $H_2O$) were used as controls. To design a new nucleic acid extraction system, biocompatible diatomaceous earth powder was purchased from Sigma-Aldrich. In addition, Milli-Q water with a resistance value greater than 18 MΩ, 99% ethyl alcohol, phosphate buffered saline (PBS, 10×, pH 7.4) and streptavidin-coupled magnetic beads (Dynabeads® MyOne™ Streptavidin C1) were used.

Example 2: Experimental Equipment

The morphology of the sample was analyzed by using a field-emission scanning electron microscopy (FE-SEM, JEOL JSM-7500F). To analyze the crystal structure of the zinc oxide nanomaterial, X-ray diffraction (XRD, Scintag-SDS 2000) was performed at 40 kV voltage and 30 mA current in continuous scan 2θ mode and Fourier transform infrared spectroscopy (FT-IR) spectroscopy (Nicolet 6700) was performed to analyze the chemical properties of the sample. Raman measurements were performed by using a Renishaw from Via Raman microscope system (Renishaw, UK). In addition, for DNA extraction, a commercial QlAamp DNA/RNA mini kit (Spin Colum) was used. Centrifuge (CF-5, 100-240 Vas, 50/60 Hz, 8 W), Vortex Mixer (T5AL, 60 Hz, 30 W, 250 V) and MSH-30d stirring heater were purchased from Dortan Scientific Co. Ariamx real-time PCR system (Agilent technologies), Gene Amp PCR system 9700 (LSK), electrophoresis apparatus (Submerge-Mini), electrophoresis gel recorder (Gel documentation system) and Nanodrop 2000 (PegLab) were used for nucleic acid detection experiments.

Example 3: Cells and Pathogens

The cells used in the experiment were used as the colon cancer cell line HCT116 (ATCC CCL-247), and as pathogens, *Brucella ovis* (ATCC 25840), *Escherichia coli* (*E coli*, ATCC 25922), *Staphylococcus aureus* (*S. aureus*) and *Bacillus cereus* (*B cereus*) were used.

Example 4: Synthesis and Morphological Analysis of Zinc Oxide Nanostar

Zinc nanostar (Zno NS) crystals were synthesized in an alkaline medium by a hydrothermal method.

1 ml of 1 M zinc nitrate hexahydrate and 1 ml of 1 M CTAB were added to a flask containing 98 ml of Milli-Q water in an appropriate order and stirred (500 rpm) while heating at 90° C. for 50 minutes. Then, under stable stirring conditions, 2 ml of an ammonium hydroxide solution was added dropwise to the reaction mixture, and stirred for a few minutes until a milky white colloidal solution was formed.

The reaction temperature, reaction time and stirring speed were controlled for uniform production of zinc oxide nanostars. To control the production of the zinc oxide nanostars, the reaction flask in an ice box was immediately taken out, centrifuged, dried at room temperature and washed with Milli-Q water. All synthesis was performed without special treatment, and finally the samples were stored in ethanol (99%).

Referring to FIG. 1, it was confirmed that (A) the zinc oxide nanostar have a particle size of 200 to 600 nm on average, and a plurality of pointed projections showed a particle shape arranged in a ring and (B) the zinc oxide nanoparticles have an average particle size of 20 to 60 nm and exhibit an irregular spherical particle shape.

Figure 2:
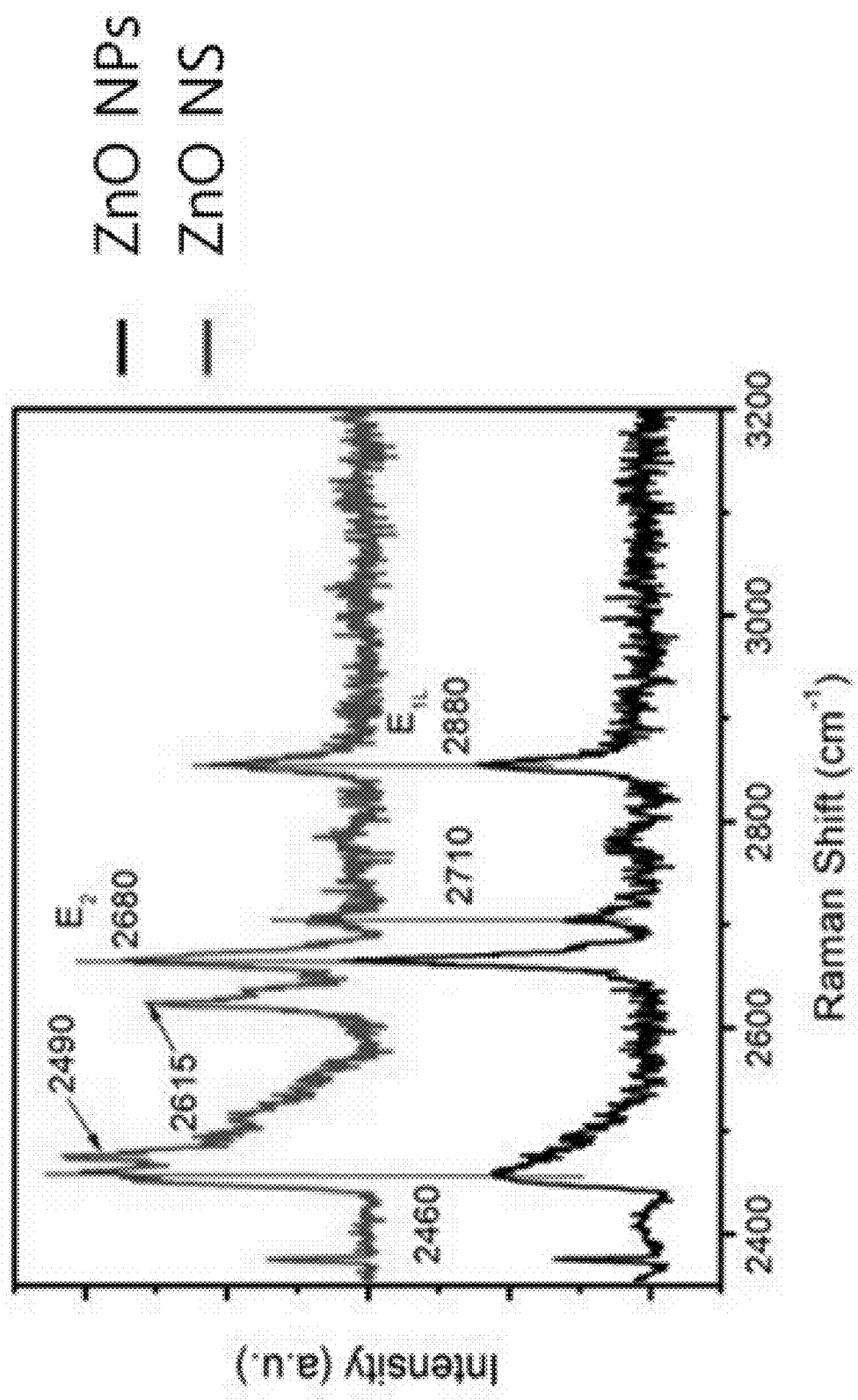
FIG. 2 shows a comparison of the structure of the zinc oxide nanostar and zinc oxide nanoparticles by Raman technique.

In addition, referring to FIG. 2, it was confirmed by Raman technique that the structures of the zinc oxide nanostar and the zinc oxide nanoparticles are different from each other.

Therefore, the zinc oxide nanostar of the present invention has a larger particle size than the conventional zinc oxide nanoparticles and has a shape of particles with a plurality of pointed projections arranged in a ring to more easily lyse the cell membranes and nucleus of the pathogens.

Example 5: Verification of Lytic Capacity of Zinc Oxide Nanostar

The commercialization kit was used for comparative analysis of the lysis properties of zinc oxide nanostars.

First, in order to lyse the sample (Brucella), AL buffer was added to 1.5 to ml of the sample, and incubated at 56° C. for 10 minutes for DNA extraction, followed by incubation at room temperature for 1 minute for RNA extraction. The prepared sample was transferred to a Qiagen column, and washing and elution steps were performed.

On the other hand, in the present invention, the conditions for extracting high-quality nucleic acids in bulk using zinc oxide nanostars instead of the commercialized AL buffer were optimized, and the extraction method was simplified.

The amount and purity of the extracted nucleic acid were measured by an Ariamx real-time PCR system, Gene Amp PCR system 9700, electrophoresis device, electrophoresis gel recording device and Nanodrop 2000.

Figure 3:
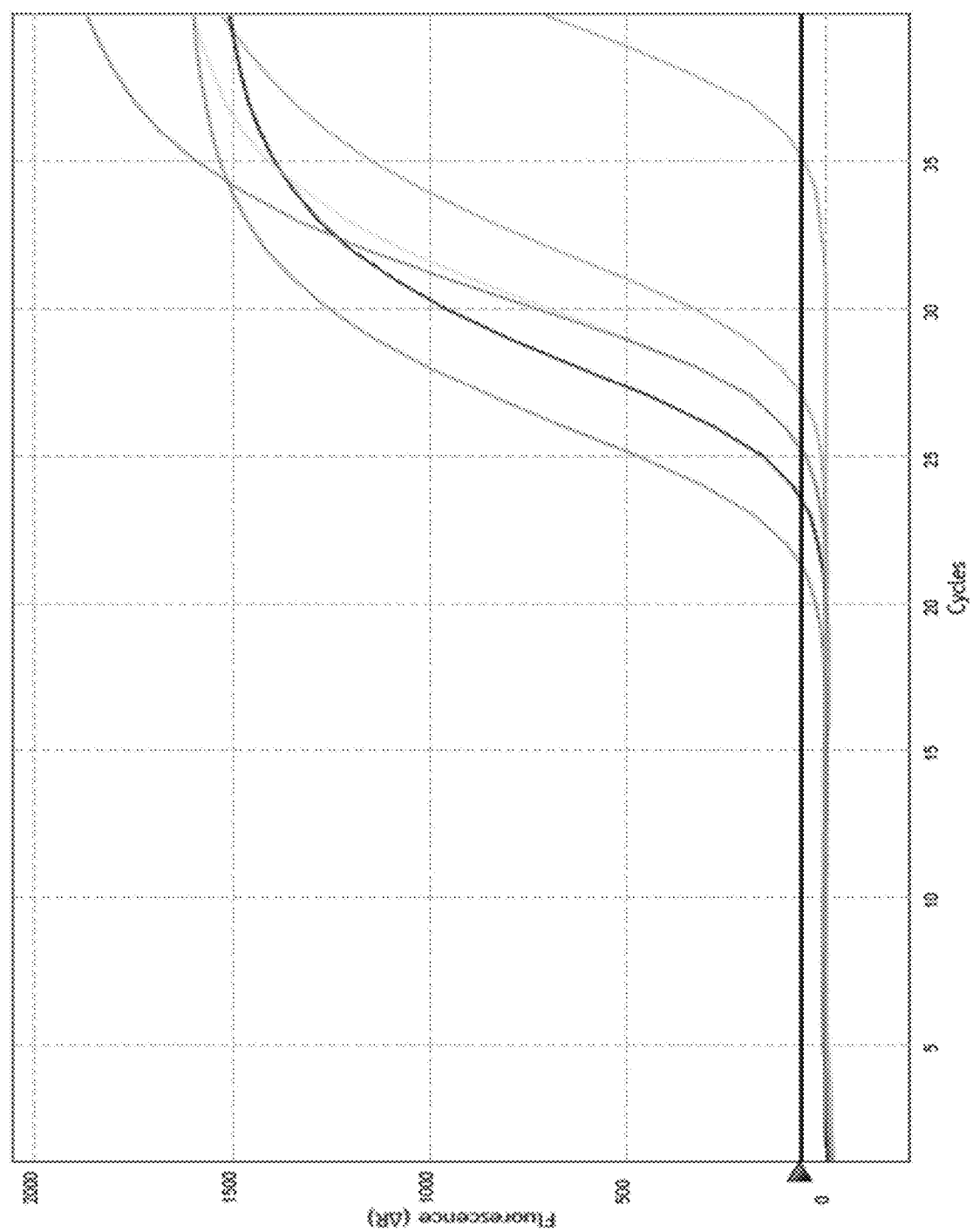
FIG. 3 shows a comparison of the lytic capacity and nucleic acid extraction efficiency of zinc oxide nanostar using *Brucella* bacteria with zinc oxide nanoparticles and a conventional nucleic acid extraction kit (Qiagen).

As for the nucleic acid extraction of Brucella, FIG. 3 and Table 1 show a comparison of the lytic capacity by extract the nucleic acid under the conditions of the conventional nucleic acid extraction kit (Qiagen)+lysis buffer used, zinc oxide nanoparticles+lysis buffer not used, zinc oxide nanostar+lysis buffer not used, conventional nucleic acid extraction kit (Qiagen)+lysis buffer not used and thus it was confirmed that the nucleic acid extraction of the zinc oxide nanostar of the present invention is most excellent.

TABLE 1

| Cq (ΔR) | Tm Product 1 (−R'(T)) | 10^5 *Brucella* (RT) |
|---|---|---|
| 23.74 | 81.5 | Qiagen + Lysis buffer |
| 25.38 | 81.5 | Zinc oxide nanoparticles (RT) |
| 21.5 | 81.5 | Zinc oxide nanostar (RT) |
| 25.45 | 81 | Qiagen |
| 35.4 | 83.5 | Negative control |

In addition, in the same manner as the above method, the lysis properties of zinc oxide nanostars were compared and analyzed using *Brucella, E. coli, Staphylococcus aureus* and *Bacillus cereus*.

Figure 4:
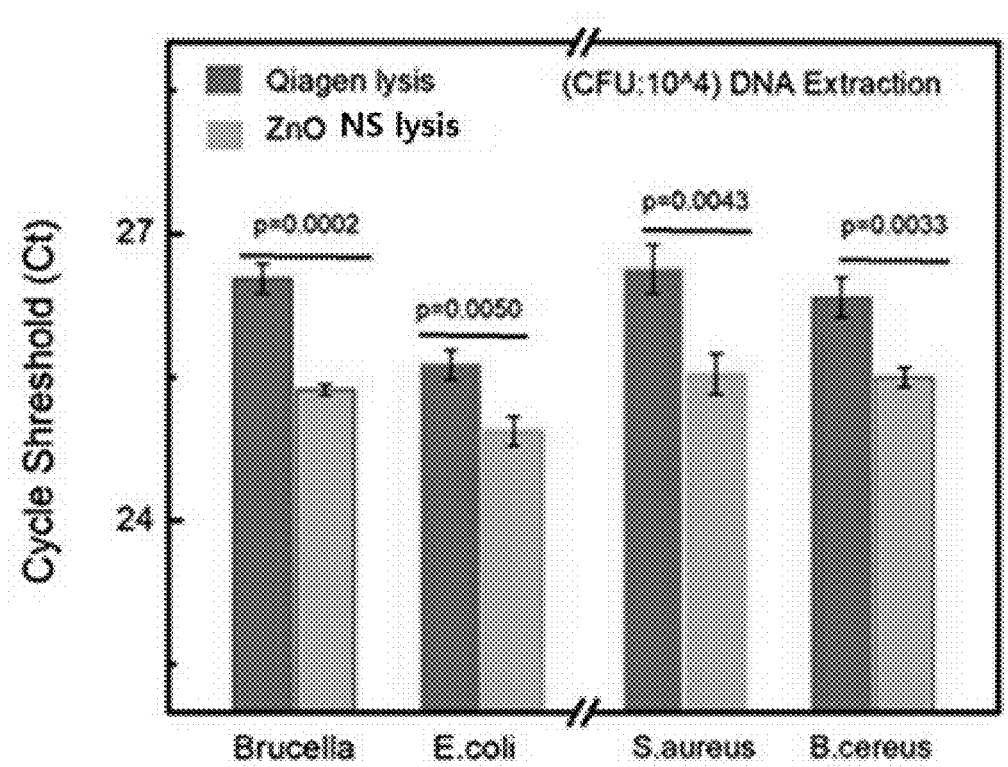
FIG. 4 shows a comparison of the lytic capacity and nucleic acid extraction efficiency of zinc oxide nanostars using *Brucella, E. coli, Staphylococcus aureus* and *Bacillus cereus* with those of a conventional nucleic acid extraction kit (Qiagen).

As a result, referring to FIG. 4, it was confirmed that the zinc oxide nanostar of the present invention has better lytic capacity and nucleic acid extraction than the conventional nucleic acid extraction kit in all four types of bacteria.

Figure 5:
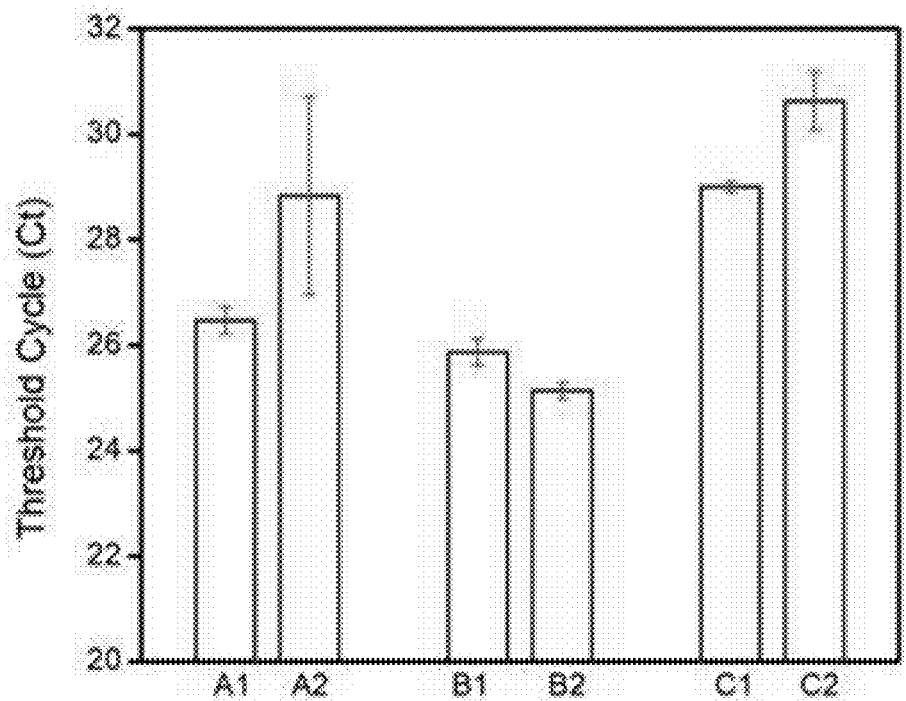
FIG. 5 confirms that it is possible to extract nucleic acid extraction by applying zinc oxide nanostar to a column of a conventional nucleic acid extraction kit (Qiagen).

In addition, FIG. 5 analyzes whether the zinc oxide nanostar of the present invention can extract the nucleic acid by applying to a conventional nucleic acid extraction kit (Qiagen) column. As a result of comparing the nucleic acid extraction efficiency by changing the conditions as shown in Table 2 below, it was confirmed that the zinc oxide nanostar can efficiently extract nucleic acid even at room temperature without a heating step.

TABLE 2

|  | A1 | A2 | B1 | B2 | C1 | C2 |
|---|---|---|---|---|---|---|
| Nucleic acid extraction composition | Qiagen | Qiagen | Qiagen + Zinc oxide nanostar | Qiagen + Zinc oxide nanostar | Qiagen | Qiagen |

TABLE 2-continued

|  | A1 | A2 | B1 | B2 | C1 | C2 |
|---|---|---|---|---|---|---|
| Lysis buffer | Used | Used | Not used | Not used | Not used | Not used |
| Temperature (° C.) | 56 | Room temperature | 56 | Room temperature | 56 | Room temperature |
| time (min) | 10 | 10 | 10 | 10 | 10 | 10 |

Example 6: Verification of Lytic Capacity of Functionalized Diatomaceous Earth and Optical Zinc Oxide Nanostar for Single Tube Nucleic Acid Extraction To further analyze the lysis properties of zinc oxide nanostars, a single tube nucleic acid extraction system was used, which was performed with reference to previous papers (Biosensors and Bioelectronics 99 (2018) 443-449.).

Briefly, (1) because the pore structure of diatomaceous earth can accommodate various molecules and the high-density silanol group on the wall is advantageous for linking with functional amine groups, the washed diatomaceous earth was functionalized with APTES. The detailed experimental process is as follows.

i) 2 ml of APTES was added dropwise to 100 ml of 95% ethanol solution and stirred at 400 rpm for 3 minutes at room temperature.

ii) 500 mg of the washed diatomaceous earth was dispersed in the solution for 4 hours at 600 rpm.

iii) After modification, the precipitate was washed twice with ethanol to remove free silanol.

iv) The diatomaceous earth functionalized with APTES was obtained by centrifuging and dried under vacuum overnight at room temperature.

v) Finally, the diatomaceous earth functionalized with APTES was dispersed in distilled water at a concentration of 50 mg/ml.

The properties of diatomaceous earth and pure diatomaceous earth functionalized with APTES were analyzed by field emission scanning electron microscopy, Fourier transform infrared spectroscopy and Raman microscopy systems.

(2) Based on the above modification, diatomaceous earth functionalized with APTES and an imidoester crosslinking agent (dimethyl suberimidate•2 HCl, DMS) were added to a 5 ml tube containing a prepared biological sample to extract nucleic acids. The detailed experimental process is as follows.

i) 100 µl of sample solution was added to a 1.5 ml tube containing 10 µl of protease K and 10 µl of lysis buffer (M-SDS lysis buffer or zinc oxide nanostar solution), mixed using a pipette and incubated at room temperature for 1 minute. 10 µl of DNase was added for RNA extraction.

ii) Thereafter, 2 mg/ml of diatomaceous earth-APTES was added and then 100 µl of 100 mg/ml DMS solution was added.

iii) After mixing, it was incubated for 10 minutes at 56° C. to dissolve M-SDS or incubated for 2 minutes at room temperature with mixing by a pipette for the lysis of zinc oxide nanostar.

iv) After incubation, the supernatant was removed and the precipitate was washed twice with 200 µl of PBS.

v) Finally, 60 µl of elution buffer (pH~10.6 NaHCO$_3$) was added and incubated for 1 minute at room temperature.

vi) After centrifugation, the supernatant was transferred to a 1.5 ml tube, and the extracted DNA or RNA was stored at −20° C.

The amount and purity of the extracted nucleic acid were measured by an Ariamx real-time PCR system, Gene Amp PCR system 9700, electrophoresis device, electrophoresis gel recording device, and Nanodrop 2000.

Figure 6:
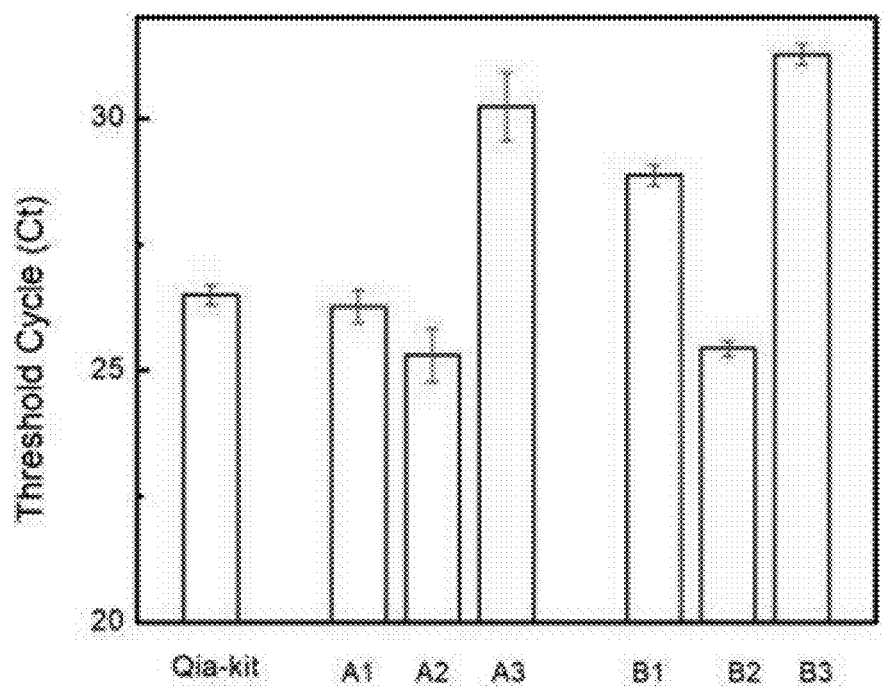
FIG. 6 confirms that it is possible to extract nucleic acid by applying zinc oxide nanostar to diatomaceous earth or homobifunctional imidoester.

FIG. 6 analyses whether the zinc oxide nanostars of the present invention can be applied to a diatomaceous earth functionalized with APTES and homobifunctional imidoesters [dimethyl adipimidate (DMA), dimethyl pimelimidate (DMP), dimethyl suberimidate (DMS) or dimethyl 3,3'-dithiobispropionimidate (DTBP)].

The zinc oxide nanostar of the present invention is applied to diatomaceous earth functionalized with APTES and DMS and as shown in Table 3 below, the nucleic acid extraction efficiency is compared in the various conditions and it is confirmed that the zinc oxide nanostar can extract nucleic acid efficiently even at normal temperature without a heating step. In addition, since the lysis buffer is not used, it is considered that the nucleic acid is less damaged and can be used for detection techniques through final PCR.

TABLE 3

|  | Qiagen | A1 | A2 | A3 | B1 | B2 | B3 |
|---|---|---|---|---|---|---|---|
| Lysis buffer | Used | Used | Zinc oxide nanostar | Not used | Used | Zinc oxide nanostar | Not used |
| Temperature (° C.) | 56 | 56 | 56 | 56 | Room temperature | Room temperature | Room temperature |
| Time (min) | 10 | 10 | 10 | 10 | 2 | 2 | 2 |

In addition, referring to FIG. 7 and Table 4, the nucleic acid extraction efficiency according to particle size was compared and the nucleic acid extraction efficiency of zinc oxide nanostar having a particle size of 350 to 900 nm was the best, and particularly, it was confirmed that the zinc oxide nanostar having a particle size of 500 nm was the optimal condition.

TABLE 4

| Cq (ΔR) | Tm Product 1 (−R'(T)) | HCT 116 10^4/ml 100 µl (60 µl DNA) |
|---|---|---|
| 26.63 | 85 | ~20 nm Zinc oxide nanoparticles |
| 26.2 | 85 | ~100 nm Zinc oxide nanostar |
| 25.75 | 90 | ~350 nm Zinc oxide nanostar |
| 25.21 | 85.5 | ~500 nm Zinc oxide nanostar |

TABLE 4-continued

| Cq (ΔR) | Tm Product 1 (−R'(T)) | HCT 116 10^4/ml 100 μl (60 μl DNA) |
|---|---|---|
| 25.25 | 85.5 | ~900 nm Zinc oxide nanostar |
| 27.21 | 85 | ~1000 nm Zinc oxide nanostar |
| 30.78 | 85 | Negative control |

Example 7: Nucleic Acid Extraction Method Using Zinc Oxide Nanostar 7-1. Synthesis of Zinc Oxide Nanostar Zinc oxide nanostar was synthesized by hydrothermal method in alkaline medium.

i) 1 ml of 1 M zinc nitrate hexahydrate and 1 ml of 1 M CTAB were added to a flask containing 98 ml of Milli-Q water in a proper sequence, and stirred while heating at 90° C. for 50 minutes (500 rpm).

ii) Then, under stable stirring conditions, 2 ml of an ammonium hydroxide solution was added dropwise to the reaction mixture and stirred for several minutes until a milky white colloidal solution was formed.

For uniform production of zinc oxide nanostars, the reaction temperature, reaction time and stirring speed were adjusted.

iii) To control the production of zinc oxide nanostars, the reaction flask in an ice box was immediately taken out and centrifuged, dried at room temperature and washed with Milli-Q water. All synthesis was performed without special treatment, and finally the samples were stored in ethanol (99%).

7-2. Nucleic Acid Extraction Method Using Zinc Oxide Nanostar and Qiagen Kit i) Zinc oxide nanostar solution was added to a 1.5 ml tube containing 100 μl of Brucella bacteria (CFU: 10^5/ml) and gently mixed within 10 minutes at room temperature using a pipette.

ii) Subsequently, the prepared sample was transferred to a Qiagen column and after washing, the DNA was eluted with 60 μl of Qiagen elution buffer.

7-3. Nucleic Acid Extraction Method Using Zinc Oxide Nanostar, Diatomaceous Earth-APTES and Imidoester i) 100 μl of Brucella was added to a 1.5 ml tube containing 10 μl of protease K and 10 μl of lysis buffer (M-SDS lysis buffer or zinc oxide nanostar solution), mixed using a pipette and incubated at room temperature for 1 minute. 10 μl of DNase was added for RNA extraction.

ii) Then, 2 mg/ml of diatomaceous earth-APTES (50 mg/ml, 40 μl) was added, followed by 100 μl of a DMS solution at a concentration of 100 mg/ml. After mixing, the mixture was incubated at 56° C. for 10 minutes for M-SDS dissolution or mixed by a pipette for dissolving zinc oxide nanostars and incubated for 2 minutes at room temperature.

iii) After incubation, the supernatant was removed and the precipitate was washed twice with 200 μl of PBS.

iv) Finally, 60 μl of elution buffer (pH~10.6 NaHCO$_3$) was added and incubated for 1 minute at room temperature.

7-4. Real-Time PCR for DNA Extraction Efficiency Analysis

It was performed in a 96 well plate using 5 μl of template (NA).

i) 20 μl of master mix was dispensed into each well of a 96 well plate using a multi-channel pipette.

ii) 5 μl of template (NA) was added to the master mix and mixed well with a pipette.

iii) An optical strip lid was placed in the well so as to avoid cross contamination and be careful not to stain the surface of the lid.

iv) A 96 well plate was centrifuged at 2000 rpm for 1 minute.

v) The 96 well plate was placed in the correct direction on the qPCR machine, and real-time PCR was performed under the following conditions.

Step 1: 95° C., 10 minutes

Step 2: 95° C., 10 seconds; 60° C., 20 seconds; 72° C., 20 seconds (40 to 45 cycles)

Step 3: 72° C., 10 minutes vi) Data analysis was performed.

Example 8: Verification of Lytic Capacity of Zinc Oxide Nanostars Using Eukaryotic Cells To verify the usability of zinc oxide nanostar in eukaryotic cells, after serial dilution of HCT116 cells, a colon cancer cell line, to a concentration of 1 to $10^4$ cells/100 μl, the extraction efficiency of DNA and RNA was analyzed using zinc oxide nanostar and zinc oxide nanoparticles and a conventional nucleic acid extraction kit (Qiagen).

Figure 8:
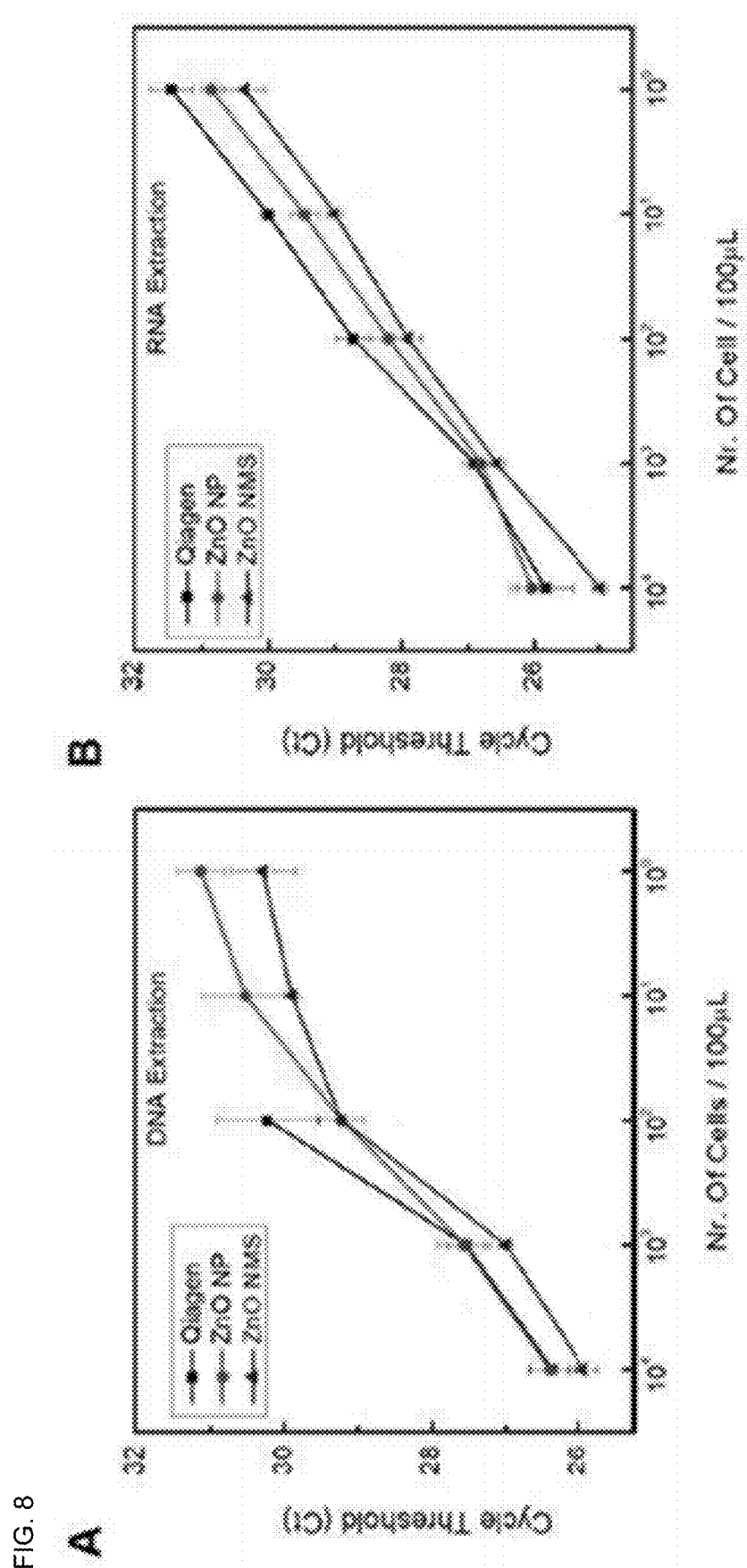
FIG. 8 shows a comparison of (A) DNA extraction and (B) RNA extraction efficiency of the conventional nucleic acid extraction kit (Qiagen), zinc oxide nanostar and zinc oxide nanoparticles using colon cancer cell line HCT116.

As a result, referring to FIG. 8, when the zinc oxide nanostar of the present invention was used under optimized conditions, it was confirmed that both DNA and RNA were detected to 1 cell/ml. The detection limit of the zinc oxide nanostar was 100 times better for DNA and 10 times better for RNA than the conventional nucleic acid extraction kits.

In addition, as a result of comparing the cell lysis capacity of the zinc oxide nanostar and the zinc oxide nanoparticle, it was confirmed that the zinc oxide nanostar detected DNA and RNA 1 to 1.5 cycles faster than the zinc oxide nanoparticle (20 nm).

In addition, zinc oxide nanostar extracted nucleic acid with higher concentration and higher purity than the conventional nucleic acid extraction kits, and RNA was extracted with high concentration and high purity even in a small number of cells (3.5±2.3 ng/μl and 1.73±0.26 ng/μl at $10^1$ cells/100 μl).

Zinc oxide nanostar enables rapid cell lysis at room temperature without the use of lysis buffer in various types of cells, and can be useful as a diagnostic system in a clinical environment.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The scope of the present invention is indicated by the following claims, and all changes or modifications derived from the meaning and scope of the claims and equivalent concepts should be interpreted to be included in the scope of the present invention.

The invention claimed is:

1. A method for extracting nucleic acid comprising:
a first step of preparing a mixture by adding zinc oxide nanostar to a nucleic acid sample and reacting;
a second step of preparing a reaction mixture by adding a diatomaceous earth modified with a silane compound to the mixture and adding at least one selected from the group consisting of dimethyl adipimidate (DMA), dimethyl pimelimidate (DMP), dimethyl suberimidate (DMS) and dimethyl 3,3'-dithiobispropionimidate (DTBP); and
a third step of extracting the nucleic acid from the reaction mixture, wherein the zinc oxide nanostar has an average particle size of 200 to 600 nm and a plurality of pointed projections showed a particle shape arranged in a ring.

2. The method for extracting nucleic acid of claim 1, wherein the silane compound is a compound represented by Chemical Formula 1:

[Chemical Formula 1]

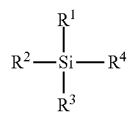

wherein each of $R^1$ to $R^3$ may be same or different, and are any one of C1 to C4 alkyl or C1 to C4 alkoxy, and $R^4$ is anyone of amino(C1 to C10) alkyl, 3-(2-amino (C1 to C4)alkylamino) (C1 to C4)alkyl or 3-[2-(2-amino (C1 to C4)alkylamino) (C1 to C4) alkylamino] (C1 to C4)alkyl.

3. The method for extracting nucleic acid of claim 2, wherein the silane compound is at least one selected from the group consisting of (3-aminopropyl) triethoxysilane (APTES), (3-aminopropyl)trimethoxysilane), (1-aminomethyl)triethoxysilane, (2-aminoethyl)triethoxysilane, (4-aminobutyl)triethoxysilane), (5-aminopentyl)triethoxysilane, (6-aminohexyl)triethoxysilane, 3-aminopropyl(diethoxy)methylsilane (APDMS), N-[3-(trimethoxysilyl)propyl]ethylenediamine, N-[3-(trimethoxysilyl)propyl] diethylenetriamine, [3-(2-aminoethylamino)propyl] trimethoxysilane (AEAPTMS) and 3-[(trimethoxysilyl) propyl]diethylenetriamine (TMPTA).

* * * * *